US012622756B2

(12) United States Patent
Rosenberg

(10) Patent No.: US 12,622,756 B2
(45) Date of Patent: May 12, 2026

(54) DISTAL END ASSEMBLY GUIDANCE

(71) Applicant: Biosense Webster (Israel) Ltd.,
Yokneam (IL)

(72) Inventor: Avigdor Rosenberg, Kiryat Tivon (IL)

(73) Assignee: Biosense Webster (Israel) Ltd.,
Yokneam (IL)

( * ) Notice: Subject to any disclaimer, the term of this
patent is extended or adjusted under 35
U.S.C. 154(b) by 231 days.

(21) Appl. No.: 18/524,530

(22) Filed: Nov. 30, 2023

(65) Prior Publication Data

US 2024/0099785 A1 Mar. 28, 2024

Related U.S. Application Data

(62) Division of application No. 17/168,123, filed on Feb.
4, 2021, now Pat. No. 11,864,844.

(Continued)

(51) Int. Cl.
*A61B 34/20* (2016.01)
*A61B 17/00* (2006.01)
(Continued)

(52) U.S. Cl.
CPC .......... *A61B 34/20* (2016.02); *A61B 18/1492*
(2013.01); *A61B 90/37* (2016.02);
(Continued)

(58) Field of Classification Search
CPC ..... A61B 34/20; A61B 90/37; A61B 18/1492;
A61B 2034/2053; A61B 2090/065;
(Continued)

(56) References Cited

U.S. PATENT DOCUMENTS 5,078,714 A 1/1992 Katims
5,341,807 A 8/1994 Nardella
(Continued)

FOREIGN PATENT DOCUMENTS

CA 2285342 A1 10/1998
JP 2013233436 A 11/2013
(Continued)

OTHER PUBLICATIONS

Partial European Search Reported dated May 23, 2022, from
corresponding EP Application No. 21216522.9.
(Continued)

*Primary Examiner* — Linda C Dvorak
*Assistant Examiner* — Abigail Bock

(57) ABSTRACT

In one embodiment, a catheter alignment system includes a
catheter to be inserted into a body part, and including
catheter electrodes to contact tissue at respective locations
within the body part, a display, and processing circuitry to
receive signals provided by the catheter, assess respective
levels of contact of ones of the catheter electrodes with the
tissue of the body part responsively to the received signals,
find a direction in which the catheter should be moved to
improve at least one of the respective levels of contact of at
least one of the catheter electrodes responsively to the
respective levels of contact of the ones of the catheter
electrodes, and render to the display a representation of the
catheter responsively to the received signals, and a direction
indicator indicating the direction in which the catheter
should be moved responsively to the found direction.

20 Claims, 8 Drawing Sheets

Related U.S. Application Data

(60) Provisional application No. 63/129,475, filed on Dec. 22, 2020.

(51) Int. Cl.

| | |
|---|---|
| *A61B 18/00* | (2006.01) |
| *A61B 18/14* | (2006.01) |
| *A61B 90/00* | (2016.01) |
| *A61M 25/01* | (2006.01) |

(52) U.S. Cl.
CPC .............. *A61B 2017/00119* (2013.01); *A61B 2017/00336* (2013.01); *A61B 2018/0022* (2013.01); *A61B 2018/00357* (2013.01); *A61B 2018/00577* (2013.01); *A61B 2034/2053* (2016.02); *A61B 2090/065* (2016.02); *A61M 2025/0166* (2013.01)

(58) Field of Classification Search
CPC ........... A61B 2017/00119; A61B 2017/00336; A61B 2018/0022; A61B 2018/00357; A61B 2018/00577; A61M 2025/0166
See application file for complete search history.

(56) References Cited

U.S. PATENT DOCUMENTS

| | | | |
|---|---|---|---|
| 5,391,199 | A | 2/1995 | Ben-Haim |
| 5,447,529 | A | 9/1995 | Marchlinski et al. |
| 5,469,857 | A | 11/1995 | Laurent et al. |
| 5,662,108 | A | 9/1997 | Budd et al. |
| 5,673,704 | A | 10/1997 | Marchlinski et al. |
| 5,836,874 | A | 11/1998 | Swanson et al. |
| 5,836,990 | A | 11/1998 | Li |
| 5,891,095 | A | 4/1999 | Eggers et al. |
| 5,935,079 | A | 8/1999 | Swanson et al. |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 7,756,576 | B2 | 7/2010 | Levin |
| 7,848,787 | B2 | 12/2010 | Osadchy |
| 7,869,865 | B2 | 1/2011 | Govari et al. |
| 9,168,004 | B2 | 10/2015 | Gliner et al. |
| 2002/0010392 | A1 | 1/2002 | Desai |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2007/0100332 | A1 | 5/2007 | Paul et al. |
| 2009/0093806 | A1 | 4/2009 | Govari et al. |
| 2009/0138007 | A1 | 5/2009 | Govari et al. |
| 2010/0204598 | A1 | 8/2010 | Desai |
| 2013/0085416 | A1 | 4/2013 | Mest |
| 2014/0018788 | A1* | 1/2014 | Engelman .......... A61B 18/1492 606/33 |
| 2014/0358079 | A1* | 12/2014 | Fischell ............ A61M 25/0084 604/113 |
| 2018/0263688 | A1 | 9/2018 | Barrish et al. |
| 2020/0022653 | A1 | 1/2020 | Moisa |
| 2020/0107877 | A1 | 4/2020 | Koblish et al. |
| 2021/0113822 | A1 | 4/2021 | Beeckler et al. |

FOREIGN PATENT DOCUMENTS

| | | | |
|---|---|---|---|
| JP | 2013233438 | A | 11/2013 |
| JP | 2017109101 | A | 6/2017 |
| JP | 2019513532 | A | 5/2019 |
| JP | 2019103809 | A | 6/2019 |
| JP | 2020516371 | A | 6/2020 |
| JP | 2021065703 | A | 4/2021 |
| WO | 9605768 | A1 | 2/1996 |
| WO | 2017184628 | A1 | 10/2017 |

OTHER PUBLICATIONS

Extended European Search Reported dated Aug. 23, 2022, from corresponding EP Application No. 21216522.9.

Search Report with English translation dated May 28, 2025, from corresponding Japanese Publication Application No. 2021-206833.

Notice of Reasons for Refusal with English translation dated Jul. 1, 2025, from corresponding Japanese Publication Application No. 2021-206833.

Written Opinion with English translation dated Sep. 26, 2025, from corresponding Japanese Publication Application No. 2021-206833.

Exam Report dated Oct. 1, 2025, from corresponding Eurpean Application No. 21216522.9.

* cited by examiner

300

RECEIVE SIGNALS PROVIDED BY THE CATHETER — 302

ACCESS RESPECTIVE LEVELS OF CONTACT OF CATHETER ELECTRODES — 304

FIND DIRECTION IN WHICH THE CATHETER SHOULD BE MOVED — 306

COMPUTE ELECTRODE CONTACT LEVEL CENTER OF MASS — 308

COMPUTE POSITION-BASED CENTER OF MASS — 310

RENDER A (2D/3D) REPRESENTATION OF THE CATHETER AND DIRECTION INDICATOR (IN 2D/3D SPACE) — 312

DISTAL END ASSEMBLY GUIDANCE

RELATED APPLICATION INFORMATION

This application is a divisional of prior filed U.S. patent application Ser. No. 17/168,123 filed on Feb. 4, 2021, which claims benefit of U.S. Provisional Patent Application No. 63/129,475 filed on Dec. 22, 2020, which prior application is hereby incorporated by reference as if set forth in full into this application.

FIELD OF THE INVENTION

The present invention relates to medical systems, and in particular, but not exclusively to, catheters with expandable distal end assemblies.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178, whose disclosures are all incorporated herein by reference (see also the Appendix of prior filed Provisional Patent Application Ser. 63/129,475 filed on Dec. 22, 2020). Locations may also be tracked using impedance or current based systems.

One medical procedure in which these types of probes or catheters have proved extremely useful is in the treatment of cardiac arrhythmias Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied to the tip electrode(s) of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

Therefore, when placing an ablation or other catheter within the body, particularly near the endocardial tissue, it is desirable to have the distal tip of the catheter in direct contact with the tissue. The contact can be verified, for example, by measuring the contact between the distal tip and the body tissue. U.S. Patent Application Publication Nos. 2007/0100332, 2009/0093806 and 2009/0138007, whose disclosures are incorporated herein by reference (see also the Appendix of priority Provisional Patent Application Ser. No. 63/129,475 filed on Dec. 22, 2020) describe methods of sensing contact pressure between the distal tip of a catheter and tissue in a body cavity using a force sensor embedded in the catheter.

A number of references have reported methods to determine electrode-tissue contact, including U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342. A number of these references, e.g., U.S. Pat. Nos. 5,935,079, 5,836,990, and 5,447,529 determine electrode-tissue contact by measuring the impedance between the tip electrode and a return electrode. As disclosed in the '529 patent, it is generally known than impedance through blood is generally lower that impedance through tissue. Accordingly, tissue contact has been detected by comparing the impedance values across a set of electrodes to premeasured impedance values when an electrode is known to be in contact with tissue and when it is known to be in contact only with blood.

U.S. Pat. No. 9,168,004 to Gliner, at al., which is herein incorporated by reference (see also the Appendix of priority Provisional Patent Application Ser. No. 63/129,475 filed on Dec. 22, 2020), describes using machine learning to determine catheter electrode contact. The '004 Patent describes cardiac catheterization being carried out by memorizing a designation of a contact state between an electrode of the probe and the heart wall as an in-contact state or an out-of-contact state, and making a series of determinations of an impedance phase angle of an electrical current passing through the electrode and another electrode, identifying maximum and minimum phase angles in the series, and defining a binary classifier adaptively as midway between the extremes. A test value is compared to the classifier as adjusted by a hysteresis factor, and a change in the contact state is reported when the test value exceeds or falls below the adjusted classifier.

US Patent Publication 2013/0085416 of Mest, which is herein incorporated by reference (see also the Appendix of priority Provisional Patent Application Ser. No. 63/129,475 filed on Dec. 22, 2020), describes a method for the in vivo re-calibration of a force sensing probe such as an electrophysiology catheter which provides for the generation of an auto zero zone. The distal tip of the catheter or other probe is placed in a body cavity within the patient.

Verification that there is no tissue contact is made using electrocardiogram (ECG) or impedance data, fluoroscopy or other real-time imaging data and/or an electro-anatomical mapping system. Once verification that there is no tissue contact made, the system recalibrates the signal emanating from the force sensor setting it to correspond to a force reading of zero grams and this recalibrated baseline reading is used to generate and display force readings based on force sensor data.

SUMMARY

There is provided in accordance with still another embodiment of the present disclosure, a catheter alignment system, including a catheter configured to be inserted into a body part of a living subject, and including catheter electrodes configured to contact tissue at respective locations within the body part, a display, and processing circuitry configured to receive signals provided by the catheter, assess respective levels of contact of ones of the catheter electrodes with the tissue in the body part responsively to the received signals, find a direction in which the catheter should be moved to improve at least one of the respective levels of contact of at least one of the catheter electrodes responsively to the respective levels of contact of the ones of the catheter electrodes, and render to the display a representation of the catheter responsively to the received signals, and a direction indicator indicating the direction in which the catheter should be moved responsively to the found direction.

Further in accordance with an embodiment of the present disclosure the catheter includes an expandable distal end assembly on which the catheter electrodes are disposed.

Still further in accordance with an embodiment of the present disclosure the expandable distal end assembly includes an inflatable balloon having an axis around which the catheter electrodes are disposed.

Additionally in accordance with an embodiment of the present disclosure the expandable distal end assembly includes an axis around which the catheter electrodes are disposed, the representation of the catheter including a two-dimensional (2D) representation of the expandable distal end assembly showing a representation of all of the catheter electrodes disposed around the axis with each of the catheter electrodes extending from a central region of the 2D representation towards an outer perimeter of the 2D representation.

Moreover, in accordance with an embodiment of the present disclosure the representation of the catheter includes a three-dimensional (3D) representation of the catheter, the processing circuitry being configured to render to the display the 3D representation of the catheter with the direction indicator in 3D space indicating the direction in which the catheter should be moved in the 3D space.

Further in accordance with an embodiment of the present disclosure the processing circuitry is configured to compute an electrode contact level center of mass of ones of the catheter electrodes responsively to the respective levels of contact and position coordinates of the ones of the catheter electrodes, and find the direction in which the catheter should be moved responsively to the computed electrode contact level center of mass.

Still further in accordance with an embodiment of the present disclosure the processing circuitry is configured to compute a position-based center of mass of ones of the catheter electrodes responsively to the position coordinates of the ones of the catheter electrodes, and find the direction in which the catheter should be moved responsively to a line extending from the computed electrode contact level center of mass to the computed position-based center of mass.

Additionally, in accordance with an embodiment of the present disclosure each of the respective levels of contact is selected from respective two states of contact indicating an in-contact state with the tissue and a not-in-contact state with the tissue, and the processing circuitry is configured to compute the electrode contact level center of mass of the ones of the catheter electrodes responsively to the respective levels of contact having a same one of the two state of contact.

Moreover, in accordance with an embodiment of the present disclosure each of the respective levels of contact is selected from respective at least three states of quality of contact with the tissue, and the processing circuitry is configured to compute the electrode contact level center of mass of the ones of the catheter electrodes as a weighted electrode contact level center of mass responsively to the respective levels of contact.

Further in accordance with an embodiment of the present disclosure each of the respective levels of contact is selected from a respective sliding scale of quality of contact with the tissue, and the processing circuitry is configured to compute the electrode contact level center of mass of the ones of the catheter electrodes as a weighted electrode contact level center of mass responsively to the respective levels of contact.

There is also provided in accordance with another embodiment of the present disclosure a catheter alignment method, including inserting a catheter into a chamber of a body part a living subject such that catheter electrodes contact tissue at respective locations within the body part, receiving signals provided by the catheter, assessing respective levels of contact of ones of the catheter electrodes with the tissue in the body part responsively to the received signals, finding a direction in which the catheter should be moved to improve at least one of the respective levels of contact of at least one of the catheter electrodes responsively to the respective levels of contact of the ones of the catheter electrodes, and rendering to a display a representation of the catheter responsively to the received signals, and a direction indicator indicating the direction in which the catheter should be moved responsively to the found direction.

Still further in accordance with an embodiment of the present disclosure the catheter includes an expandable distal end assembly on which the catheter electrodes are disposed.

Additionally, in accordance with an embodiment of the present disclosure the expandable distal end assembly includes an inflatable balloon having an axis around which the catheter electrodes are disposed.

Moreover, in accordance with an embodiment of the present disclosure the representation of the catheter includes a two-dimensional (2D) representation of an expandable distal end assembly of the catheter showing a representation of all of the catheter electrodes disposed around an axis of the expandable distal end assembly with each of the catheter electrodes extending from a central region of the 2D representation towards an outer perimeter of the 2D representation.

Further in accordance with an embodiment of the present disclosure the representation of the catheter includes a three-dimensional (3D) representation of the catheter, the rendering including rendering to the display the 3D representation of the catheter with the direction indicator in 3D space indicating the direction in which the catheter should be moved in the 3D space.

Still further in accordance with an embodiment of the present disclosure, the method includes computing an electrode contact level center of mass of the ones of the catheter electrodes responsively to the respective levels of contact and position coordinates of the ones of the catheter electrodes, and wherein the finding includes finding the direction in which the catheter should be moved responsively to the computed electrode contact level center of mass.

Additionally, in accordance with an embodiment of the present disclosure, the method includes computing a position-based center of mass of the ones of the catheter electrodes responsively to the position coordinates of the ones of the catheter electrodes, and wherein the finding includes finding the direction in which the catheter should be moved responsively to a line extending from the computed electrode contact level center of mass to the computed position-based center of mass.

Moreover, in accordance with an embodiment of the present disclosure each of the respective levels of contact is selected from respective two states of contact indicating an in-contact state with the tissue and a not-in-contact state with the tissue, and the computing includes computing the electrode contact level center of mass of the ones of the catheter electrodes responsively to the respective levels of contact having a same one of the two state of contact.

Further in accordance with an embodiment of the present disclosure each of the respective levels of contact is selected from respective at least three states of quality of contact with the tissue, and the computing includes computing the electrode contact level center of mass of the ones of the catheter electrodes as a weighted electrode contact level center of mass responsively to the respective levels of contact.

Still further in accordance with an embodiment of the present disclosure each of the respective levels of contact is selected from a respective sliding scale of quality of contact with the tissue, and the computing includes computing the electrode contact level center of mass of the ones of the catheter electrodes as a weighted electrode contact level center of mass responsively to the respective levels of contact.

There is also provided in accordance with still another embodiment of the present disclosure a catheter protection system, including a sheath having a distal end, and configured to be inserted into a body part of a living subject, a catheter including a shaft having a distal portion, an expandable distal end assembly disposed distally to the distal portion, the catheter being configured to be inserted through the sheath with the distal portion and the expandable distal end assembly protruding from the sheath into the body part, the catheter including a pusher disposed in the shaft and coupled to the expandable distal end assembly such that adjusting the pusher longitudinally with respect to the shaft selectively elongates and shortens the distal end assembly, a position tracking sub-system configured to track a relative position of the distal portion of the shaft and the distal end of the sheath, and find when the distal portion of the shaft enters the distal end of the sheath responsively to the tracked relative position, and a pusher actuator configured to automatically actuate the pusher to elongate the expandable distal end assembly responsibly to the distal portion of the shaft entering the distal end of the sheath.

Additionally, in accordance with an embodiment of the present disclosure, the system includes a sound outputting device configured to provide an audible alert responsively to the distal portion of the shaft entering the distal end of the sheath.

Moreover, in accordance with an embodiment of the present disclosure the position tracking sub-system is configured to find when the distal portion of the shaft exits the distal end of the sheath responsively to the tracked relative position, and the pusher actuator is configured to automatically actuate the pusher to shorten the expandable distal end assembly responsibly to the distal portion of the shaft exiting the distal end of the sheath.

Further in accordance with an embodiment of the present disclosure, the system includes a sound outputting device configured to provide an audible alert responsively to the distal portion of the shaft exiting the distal end of the sheath.

Still further in accordance with an embodiment of the present disclosure the position tracking sub-system includes a proximal electrode disposed proximally to the expandable distal end assembly on the distal portion of the shaft, and body surface electrodes configured to be attached to a skin surface of the living subject, the position tracking sub-system being configured to track the relative position of the distal portion of the shaft and the distal end of the sheath responsively to a measured electrical impedance between the proximal electrode and the body surface electrodes.

Additionally in accordance with an embodiment of the present disclosure the position tracking sub-system includes generator coils configured to generate magnetic fields having different frequencies in the body part, a first magnetic coil sensor disposed proximally to the expandable distal end assembly at the distal portion of the shaft, and a second magnetic coil sensor disposed at the distal end of the sheath, the first and second magnetic coil sensors being configured to output respective electrical signals responsively to detecting the magnetic fields, the position tracking sub-system being configured to track the relative position of the distal portion of the shaft and the distal end of the sheath responsively to the output electrical signals.

There is also provided in accordance with still another embodiment of the present disclosure a catheter protection system, including a sheath having a distal end, and configured to be inserted into a body part of a living subject, a catheter including a shaft having a distal portion, an expandable distal end assembly disposed distally to the distal portion, the catheter being configured to be inserted through the sheath with the distal portion and the expandable distal end assembly protruding from the sheath into the body part, the catheter including a pusher disposed in the shaft and coupled to the distal end assembly such that adjusting the pusher longitudinally with respect to the shaft selectively elongates and shortens the distal end assembly, a position tracking sub-system configured to track a relative position of the distal portion of the shaft and the distal end of the sheath, and find when the distal portion of the shaft enters the distal end of the sheath responsively to the tracked relative position, and a sound outputting device configured to provide an audible alert responsibly to the distal portion of the shaft entering the distal end of the sheath.

Moreover, in accordance with an embodiment of the present disclosure the position tracking sub-system is configured to find when the distal portion of the shaft exits the distal end of the sheath responsively to the tracked relative position, and the sound outputting device is configured to provide another audible alert responsibly to the distal portion of the shaft exiting the distal end of the sheath.

Further in accordance with an embodiment of the present disclosure the position tracking sub-system includes a proximal electrode disposed proximally to the expandable distal end assembly on the distal portion of the shaft, and body surface electrodes configured to be attached to a skin surface of the living subject, the position tracking sub-system being configured to track the relative position of the distal portion of the shaft and the distal end of the sheath responsively to a measured electrical impedance between the proximal electrode and the body surface electrodes.

Still further in accordance with an embodiment of the present disclosure the position tracking sub-system includes generator coils configured to generate magnetic fields having different frequencies in the body part, a first magnetic coil sensor disposed proximally to the expandable distal end assembly at the distal portion of the shaft, and a second magnetic coil sensor disposed at the distal end of the sheath, the first and second magnetic coil sensors being configured to output respective electrical signals responsively to detecting the magnetic fields, the position tracking sub-system being configured to track the relative position of the distal portion of the shaft and the distal end of the sheath responsively to the output electrical signals.

There is also provided in accordance with still another embodiment of the present disclosure a catheter protection method, including inserting a sheath into a body part of a living subject, inserting a catheter through the sheath with a distal portion of a shaft of the catheter and an expandable distal end assembly of the catheter protruding from the sheath into the body part, adjusting a pusher disposed in the shaft, and coupled to the expandable distal end assembly, longitudinally with respect to the shaft to selectively elongate and shorten the expandable distal end assembly, tracking a relative position of the distal portion of the shaft and the distal end of the sheath, finding when the distal portion of the shaft enters the distal end of the sheath responsively to the tracked relative position, and automatically actuating the pusher to elongate the expandable distal end assembly responsibly to the distal portion of the shaft entering the distal end of the sheath.

Additionally, in accordance with an embodiment of the present disclosure, the method includes providing an audible alert responsively to the distal portion of the shaft entering the distal end of the sheath.

Moreover, in accordance with an embodiment of the present disclosure, the method includes finding when the distal portion of the shaft exits the distal end of the sheath responsively to the tracked relative position, and automatically actuating the pusher to shorten the expandable distal end assembly responsibly to the distal portion of the shaft exiting the distal end of the sheath.

Further in accordance with an embodiment of the present disclosure, the method includes provide an audible alert responsively to the distal portion of the shaft exiting the distal end of the sheath.

Still further in accordance with an embodiment of the present disclosure the tracking includes tracking the relative position of the distal portion of the shaft and the distal end of the sheath responsively to a measured electrical impedance between a proximal electrode disposed proximally to the expandable distal end assembly on the distal portion of the shaft and body surface electrodes attached to a skin surface of the living subject.

Additionally in accordance with an embodiment of the present disclosure, the method includes generating magnetic fields having different frequencies in the body part, and outputting respective electrical signals by a first magnetic coil sensor disposed proximally to the expandable distal end assembly at the distal portion of the shaft and a second magnetic coil sensor disposed at the distal end of the sheath responsively to detecting the magnetic fields, wherein the tracking includes tracking the relative position of the distal portion of the shaft and the distal end of the sheath responsively to the output electrical signals.

There is also provided in accordance with still another embodiment of the present disclosure a catheter protection method, including inserting a sheath into a body part of a living subject, inserting a catheter through the sheath with a distal portion of a shaft of the catheter and an expandable distal end assembly of the catheter protruding from the sheath into the body part, adjusting a pusher disposed in the shaft, and coupled to the expandable distal end assembly, longitudinally with respect to the shaft to selectively elongate and shorten the expandable distal end assembly, tracking a relative position of the distal portion of the shaft and the distal end of the sheath, finding when the distal portion of the shaft enters the distal end of the sheath responsively to the tracked relative position, and providing an audible alert responsibly to the distal portion of the shaft entering the distal end of the sheath.

Moreover, in accordance with an embodiment of the present disclosure, the method includes finding when the distal portion of the shaft exits the distal end of the sheath responsively to the tracked relative position, and providing another audible alert responsibly to the distal portion of the shaft exiting the distal end of the sheath.

Further in accordance with an embodiment of the present disclosure the tracking includes tracking the relative position of the distal portion of the shaft and the distal end of the sheath responsively to a measured electrical impedance between a proximal electrode disposed proximally to the expandable distal end assembly on the distal portion of the shaft and body surface electrodes attached to a skin surface of the living subject.

Still further in accordance with an embodiment of the present disclosure, the method includes generating magnetic fields having different frequencies in the body part, and outputting respective electrical signals by a first magnetic coil sensor disposed proximally to the expandable distal end assembly at the distal portion of the shaft and a second magnetic coil sensor disposed at the distal end of the sheath responsively to detecting the magnetic fields, wherein the tracking includes tracking the relative position of the distal portion of the shaft and the distal end of the sheath responsively to the output electrical signals.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
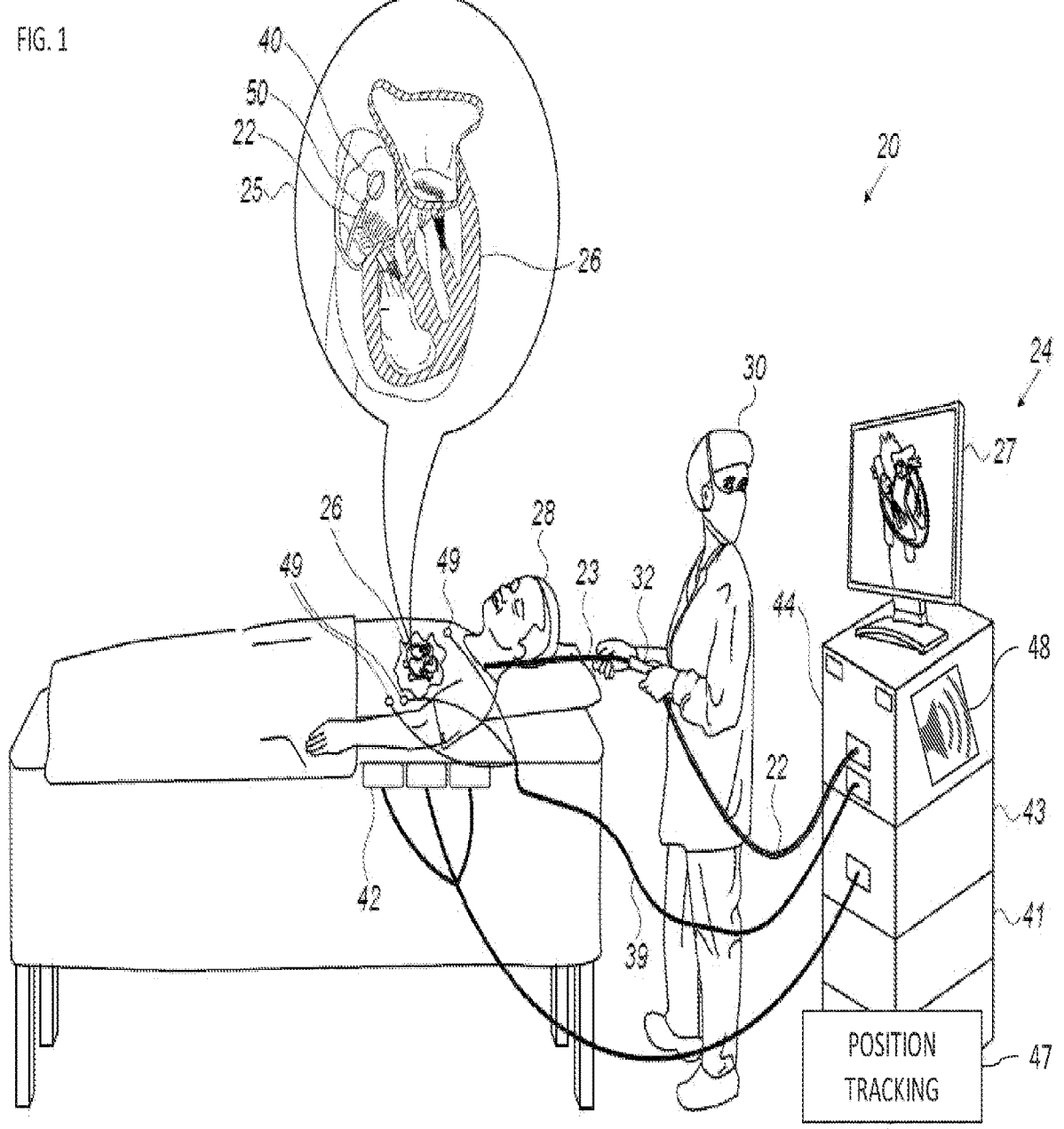
FIG. 1 is a schematic pictorial illustration of a catheter-based position tracking and ablation system in accordance with an embodiment of the present invention.

Optimal alignment and contact of all active catheter electrodes (e.g., balloon electrodes with the pulmonary vein antrum or any other body part) provides a greater probability of a successful single-shot ablation. One solution is to provide a view of the catheter electrodes indicating which electrodes are in sufficient contact with tissue using appropriate markings (e.g., highlighting the electrodes in sufficient contact). Although such a solution somewhat guides the physician how to improve contact between the electrodes and the tissue, the view is not very intuitive as to the direction of the deflection and/or manipulation action which needs to be applied to the balloon to improve the contact between the catheter electrodes and the tissue.

Therefore, embodiments of the present invention solve the above problems by providing a catheter alignment system which assesses levels of contact of catheter electrodes with tissue of a body part (e.g., chamber of a heart of a living subject), finds a direction in which the catheter should be moved to improve the level of contact of one or more of the catheter electrodes, and renders to a display, a representation of the catheter and a direction indicator (e.g., arrow) indicating the direction in which the catheter should be moved (including deflected) based on the found direction.

In some embodiments, the representation of the catheter is a two-dimensional (2D) representation showing the catheter electrodes disposed around a longitudinal axis of the catheter with each catheter electrode extending from a central region of the 2D representation towards an outer perimeter of the 2D representation.

In some embodiments, the representation includes a three-dimensional (3D) representation of the catheter with the directional indicator (e.g., arrow) indicating the direction in which the catheter should be moved in 3D space.

In some embodiments, the direction in which the catheter should be moved may be computed based on an "electrode contact level center of mass", which may be computed responsively to the position coordinates of the catheter electrodes and the assessed levels of contact of the catheter electrodes.

In some embodiments, the electrode contact level center of mass may be computed as a weighted center of mass weighted according to the different assessed levels of contact.

In some embodiments the assessed levels of contact may include two states (e.g., in-contact, not-in-contact), or multi-state (e.g., 0, 1, 2), or based on a sliding level. So for example, where two-levels of contact are used, the computation of the "electrode contact level center of mass" may be computed based on whether the electrodes are in contact or not, so that electrodes in contact are given a weight of 1 while electrodes not in contact are given a weight of 0.

In some embodiments, the direction in which the catheter should be moved may be found responsively to a line extending from the computed electrode contact level center of mass to a "position-based center of mass", which is computed without taking into account the assessed levels of contact.

When a catheter with an expandable distal end assembly, such as a balloon catheter, is inserted into a body part of a living subject, a sheath is first inserted into the body part and the catheter is inserted into the sheath with the distal end assembly in a collapsed form. Once the distal end assembly is advanced out of the sheath into the body part, the distal end assembly may then be deployed, for example, by inflating an inflatable balloon or expanding a basket. Once use of the catheter is completed in the body part the distal end assembly is collapsed and withdrawn back into the sheath and out of the living subject. In some cases, the expandable distal end assembly includes a pusher which elongates the distal end assembly to assist in collapsing it. If the distal end assembly is not collapsed prior to being withdrawn into the sheath, the distal end assembly may become damaged.

Therefore, embodiments of the present invention include a catheter protection system which automatically actuates a pusher to elongate a distal end assembly (causing the distal end assembly to collapse), and/or provides an audible warning to the physician, when a distal portion of a shaft of the catheter (more proximal than the distal end assembly) is being withdrawn into the distal end of the sheath. The distal portion of the catheter shaft being withdrawn into the distal end of the sheath may be tracked based on tracking a relative position of the distal end of the sheath and the distal portion of the catheter shaft.

The relative position of the distal end of the sheath may be tracked using any suitable method. In some embodiments, electrical impedance is used to track the relative position based on a measured electrical impedance between an electrode located on the distal portion of the catheter shaft and body surface electrodes attached to a skin surface of the living subject. The measured electrical impedance increases when the proximal electrode is withdrawn into the sheath thereby providing an indication of the relative position between the distal end of the sheath and the distal end of the shaft. In some embodiments, the distal end of the sheath and the distal portion of the shaft of the catheter each include respective position sensors, e.g., magnetic position sensors. The relative position may then be computed responsively to signals provided by the position sensors.

System Description

Figure 2:
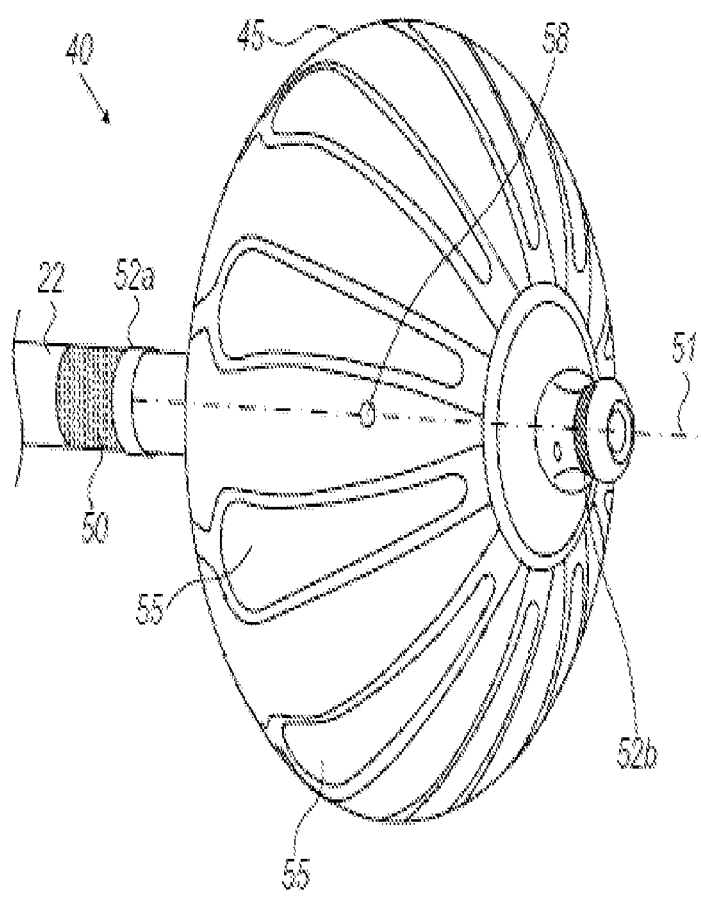
FIG. 2 is a schematic pictorial illustration of a balloon catheter used in the system of FIG. 1.

Reference is now made to FIG. 1, which is a schematic pictorial illustration of a catheter-based position tracking and ablation system 20 in accordance with an embodiment of the present invention. Reference is also made to FIG. 2, which is a schematic pictorial illustration of a balloon catheter 40, in accordance with an embodiment of the present invention.

The position tracking and ablation system 20 is used to determine the position of the balloon catheter 40, seen in an inset 25 of FIG. 1 and in more detail in FIG. 2. The balloon catheter 40 includes a shaft 22 and an inflatable balloon 45 fitted at a distal end of the shaft 22. The catheter 40 is configured to be inserted into a body part of a living subject. Typically, the balloon catheter 40 is used for therapeutic treatment, such as spatially ablating cardiac tissue, for example at the left atrium.

The position tracking and ablation system 20 can determine a position and orientation of the shaft 22 of the balloon catheter 40 based on sensing-electrodes 52 (proximal-electrode 52a disposed on the shaft 22 and distal-electrode 52b disposed at the distal end of the inflatable balloon 45) and a magnetic sensor 50 fitted just proximally to proximal-electrode 52a. The proximal-electrode 52a, the distal-electrode 52b, and the magnetic sensor 50 are connected by wires running through the shaft 22 to various driver circuitries in a console 24. In some embodiments, the distal electrode 52b may be omitted.

The shaft 22 defines a longitudinal axis 51. A center point 58 on the axis 51, which is the origin of the sphere shape of the inflatable balloon 45, defines a nominal position of the inflatable balloon 45. The catheter 40 includes multiple catheter electrodes 55 disposed on the inflatable balloon 45 or on any suitable expandable distal end assembly, around the longitudinal axis 51. In some embodiments, the catheter electrodes 55 are disposed in a circumference over the inflatable balloon 45, which occupy a large area as compared with sensing-electrodes 52a and 52b. The catheter electrodes 55 are configured to contact tissue at respective locations within the body part. Radio frequency power may be supplied to the catheter electrodes 55 to ablate the tissue, e.g., cardiac tissue.

Typically, the disposed catheter electrodes 55 are evenly distributed along an equator of the inflatable balloon 45, where the equator is generally aligned perpendicular to the longitudinal axis 51 of the distal end of the shaft 22.

The illustration shown in FIG. 2 is chosen purely for the sake of conceptual clarity. Other configurations of sensing-electrodes 52 and catheter electrodes 55 are possible. Additional functionalities may be included in the magnetic sensor 50. Elements which are not relevant to the disclosed embodiments of the invention, such as irrigation ports, are omitted for the sake of clarity.

A physician 30 navigates the balloon catheter 40 to a target location in a heart 26 of a patient 28 by manipulating the shaft 22 using a manipulator 32 near the proximal end of the catheter and/or deflection from a sheath 23. The balloon catheter 40 is inserted, while the inflatable balloon 45 is deflated, through the sheath 23, and only after the balloon catheter 40 is retracted from the sheath 23 is the inflatable balloon 45 inflated and regains its intended functional shape. By containing balloon catheter 40 in a deflated configuration, the sheath 23 also serves to minimize vascular trauma on its way to the target location.

Console 24 comprises processing circuitry 41, typically a general-purpose computer and a suitable front end and interface circuits 44 for generating signals in, and/or receiving signals from, body surface electrodes 49 which are attached by wires running through a cable 39 to the chest and to the back of the patient 28.

The system 20 includes a position tracking sub-system 47, which may comprise a magnetic-sensing sub-system at least partially disposed in the console 24. The patient 28 is placed in a magnetic field generated by a pad containing magnetic field generator coils 42, which are driven by a unit 43 disposed in the console 24. The magnetic fields generated by the coils 42 generate direction signals in the magnetic sensor 50, which are then provided as corresponding electrical inputs to the processing circuitry 41.

In some embodiments, the processing circuitry 41 uses the position-signals received from the sensing-electrodes 52 (and/or the body surface electrodes 49), the magnetic sensor 50, and the catheter electrodes 55 to estimate a position of the balloon catheter 40 inside an organ, such as inside a cardiac chamber. In some embodiments, the processing circuitry 41 correlates the position signals received from the electrodes 52, 55 with previously acquired magnetic location-calibrated position signals, to estimate the position of the balloon catheter 40 inside a cardiac chamber. The position coordinates of the sensing-electrodes 52 and the catheter electrodes 55 may be determined by the processing circuitry 41 based on, among other inputs, measured impedances, or on proportions of currents distribution, between the electrodes 52, 55 and the surface electrodes 49. The console 24 drives a display 27, which shows the distal end of the catheter position inside the heart 26.

The method of position sensing using current distribution measurements and/or external magnetic fields is implemented in various medical applications, for example, in the Carto® system, produced by Biosense Webster Inc. (Irvine, California), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1.

The Carto®3 system applies an Active Current Location (ACL) impedance-based position-tracking method. In some embodiments, using the above noted ACL method, the processing circuitry 41 estimates the positions of the sensing-electrodes 52 and the catheter electrodes 55. In some embodiments, the signals received from the electrodes 52, 55 are correlated with a matrix which maps impedance (or another electrical value) measured by the sensing-electrodes 52, 55 with a position of that was previously acquired from magnetic location-calibrated position signals.

In some embodiments, to visualize catheters which do not include a magnetic sensor, the processing circuitry 41 may apply an electrical signal-based method, referred to as the Independent Current Location (ICL) method. In the ICL method, the processing circuitry 41 calculates a local scaling factor for each voxel of a volume of the balloon catheter 40. The factor is determined using a catheter with multiple electrodes having a known spatial relationship, such as a Lasso-shaped catheter.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. The system 20 typically comprises additional modules and elements that are not directly related to the disclosed techniques, and thus are intentionally omitted from FIG. 1 and from the corresponding description. A balloon distal end assembly has been described by way of example only, and any suitable distal end assembly, e.g., a basket distal end assembly, may be used instead.

Figure 7:
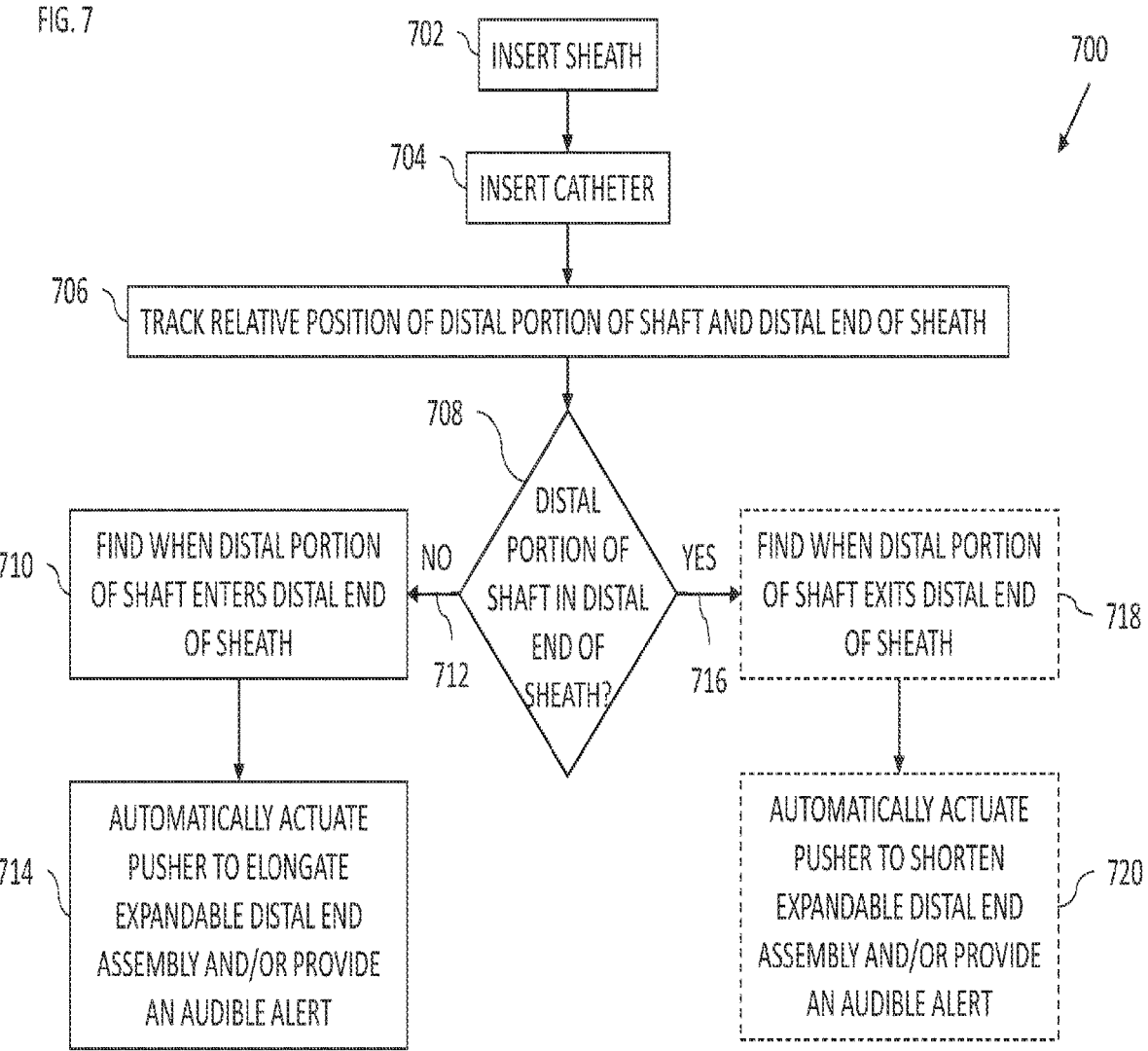
FIG. 7 is a flowchart including steps in a method for use in the system of FIG. 1.

The system 20 may also include a sound outputting device 48 configured to provide an audible alert, described in more detail with reference to FIG. 7.

Figures 3, 4:
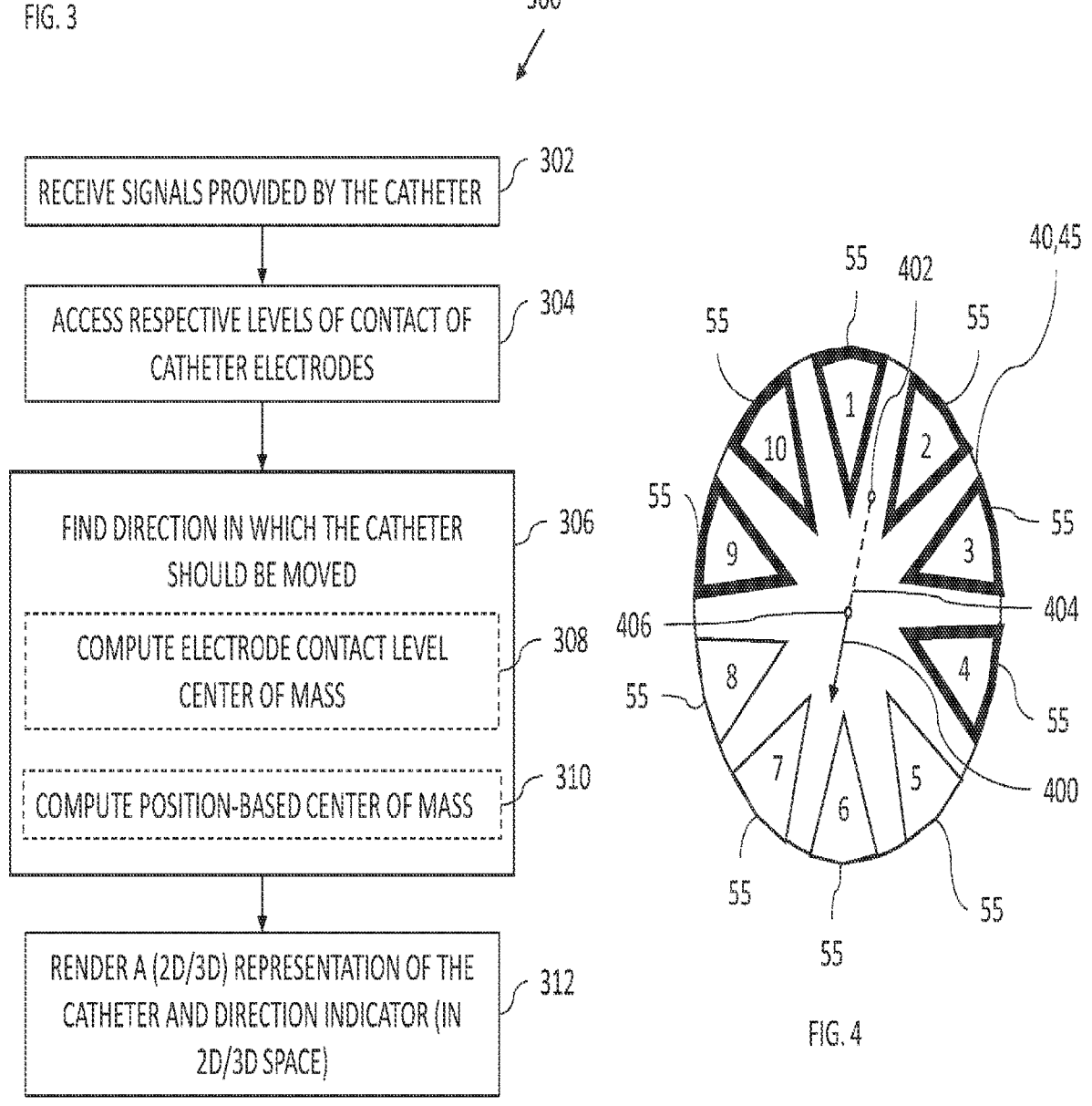
FIG. 3 is a flowchart including steps in a balloon alignment method for use in the system of FIG. 1.
FIG. 4 is a schematic view illustrating finding a direction in which to move the balloon catheter of FIG. 2.

Reference is now made to FIG. 3, which is a flowchart 300 including steps in a balloon alignment method for use in the system 20 of FIG. 1.

The processing circuitry 41 (FIG. 1) is configured to receive (block 302) signals provided by the catheter 40. The signals may be provided directly from the catheter electrodes 55 to the processing circuitry 41 or from the body surface electrodes 49 which detect the signals provided by the catheter electrodes 55, or from a force sensor or temperature sensors. The processing circuitry 41 is configured to assess (block 304) respective levels of contact of ones (some or all) of the catheter electrodes 55 with the tissue in the body part responsively to the received signals. In other words, the processing circuitry 41 assesses a level of contact for each of the catheter electrodes 55 or for each electrode of a sub-set of the catheter electrodes 55 (e.g., only active electrodes).

A level of contact may be assessed based on different methods including impedance measurements, temperature measurements, force or pressure measurements, or from analysis of IEGM traces, as will now be described in more detail.

Any one of the catheter electrodes 55 may be in full or partial contact with the tissue of the heart 26. In some cases, any one of the catheter electrodes 55 may be in contact with the tissue via another fluid such as blood of various thicknesses. The level of contact (full or partial contact, or contact via another liquid) of any one of the catheter electrodes 55 with the tissue may be assessed based on the signals provided by the catheter 40.

The term "level of contact" as used in the specification and claims is defined herein as a quantitative indicator of the degree of electrical contact between one of the catheter electrodes 55 and the tissue. The "level of contact" may be expressed directly, for example in terms a measured electrical impedance, or indirectly, for example in terms of contact force, pressure or IEGM (intracardiac electrogram) amplitude, as will now be described below in more detail.

In some embodiments, the catheter 40 may provide signals which provide an indication of impedance between the catheter electrodes 55 and body surface electrodes 49. The indication of the impedance provides an indication of a level of contact, such that a higher value of impedance between one of the catheter electrodes 55 and the body surface electrodes 49 indicates a higher level of contact between that catheter electrode 55 and the tissue. A value of impedance may be selected to define a minimum level of contact considered to represent sufficient contact between any one of the catheter electrodes 55 and the tissue.

In some embodiments, the impedance between one of the catheter electrodes 55 and another one of the electrodes on the catheter may be used as a measure of level of contact. As disclosed in the '529 patent mentioned in the background section above, it is generally known that impedance through blood is generally lower than impedance through tissue. Accordingly, tissue contact may be assessed by comparing impedance values across a set of electrodes to premeasured impedance values when an electrode is known to be in sufficient contact with tissue and when it is known to be in contact only with blood.

In some embodiments, a temperature sensor (e.g., a thermocouple) on each of the catheter electrodes 55 may be used as a measure of level of contact. The temperature sensor on each electrode 55 senses a superposition of the temperature of the irrigation fluid within the balloon 45 and the temperature of the blood or the tissue outside of the balloon. The irrigation fluid is cooler than the blood. When an electrode is not in contact with the tissue, the blood flow across the surface of the electrode is warming the electrode from the outside and the total temperature sensed by the temperature sensor of the electrode will be higher. When the electrode is touching the tissue and the blood flow is blocked, the irrigation fluid at the inside of the electrode causes the temperature sensed by the electrode to be lower.

Therefore, the temperature values, sensed on each of the electrodes 55 may be used as a measure of level of contact.

In some embodiments, the method of U.S. Pat. No. 9,168,004 to Gliner, at al., which is herein incorporated by reference (see also the Appendix of priority Provisional Patent Application Ser. No. 63/129,475 filed on Dec. 22, 2020), may be used to assess level of contact using a machine learning based method.

In some embodiments, the catheter 40 may provide signals from force or pressure sensors (not shown). The indication of force or pressure provides an indication of a level of contact, such that a higher value of force or pressure indicates a higher level of contact between one of the catheter electrodes 55 and the tissue. A value of force or pressure may be selected to define a minimum level of contact considered to represent sufficient contact between any one of the catheter electrodes 55 and the tissue. These embodiments may use any suitable force or pressure sensors as well as any suitable method for measuring the force or pressure.

In some embodiments, generated IEGM traces may be used to assess the level of contact between any one of the catheter electrodes 55 and the tissue. The maximum amplitude of the IEGM trace associated with one of the catheter electrodes 55 is indicative of the level of contact between that catheter electrode 55 and the tissue, such that a higher value of the maximum amplitude of the IEGM trace indicates a higher level of contact between that catheter electrode 55 and the tissue. An amplitude value of the IEGM trace may be selected to define a minimum level of contact considered to represent sufficient contact between any one of the catheter electrodes and the tissue.

Each of the respective levels of contact may be selected from respective two states of contact indicating an in-contact state with the tissue and a not-in-contact state with the tissue. In other words, the electrodes can have one of two states (in-contact or not-in-contact) and different electrodes may have different contact states. For example, if a measured value (e.g., impedance, temperature, or force) is lower (or higher) than a given limit, the assessed contact level may be an in-contact state, and if the measured value is higher (or lower) than the given limit, the assessed contact level may be a not-in-contact state.

In some embodiments, each of the respective levels of contact is selected from respective multiple states (e.g., at least three states) of quality of contact with the tissue (e.g., not-in-contact, in weak contact, in strong contact). For example, each state may be associated with a given limit (e.g., impedance, temperature, or force).

In some embodiments, each of the respective levels of contact is selected from a respective sliding scale of quality of contact with the tissue. For example, the levels of contact may be equal to, or proportion to, a measure of contact such as impedance, temperature, or force.

Reference is now made to FIG. 4, which is a schematic view illustrating finding a direction in which to move the balloon catheter 40 of FIG. 2. Reference is also made to FIG. 3. FIG. 4 shows a schematic view of the catheter 40 as viewed from a point along the longitudinal axis 51 (FIG. 2) more distally than the distal tip of the inflatable balloon 45. Each of the catheter electrodes 55 are labelled (e.g., 1-10) for the sake of simplicity. The electrodes 55 which have a level of contact above a given limit are highlighted with a thicker border (e.g., electrodes 1-4, and 9-10) while electrodes with a level of contact below the given limit are shown with a thinner border (e.g., electrodes 5-8).

The processing circuitry 41 (FIG. 1) is configured to find (block 306) a direction 400 in which the catheter 40 should be moved to improve the respective level(s) of contact of one or more of the catheter electrodes 55 (e.g., in a direction towards electrodes 5-8, and specifically between electrodes 6 and 7 in the example of FIG. 4) responsively to the respective assessed levels of some or all of the catheter electrodes (e.g., electrodes 1-4, and 9-10, or all of the electrodes 55).

In some embodiments, the direction 400 may be found by using a pre-populated lookup table which lists the different combinations of electrodes with levels of contact above a given level and a corresponding direction, typically referenced with respect to the longitudinal axis 51 in which to move the catheter 40. That is, the graphical user interface can indicate to the operator (textually or graphically) to move the balloon in a "direction transverse to the longitudinal axis (or central axis) of the balloon" or "in a direction towards electrodes 6 and 7".

In some embodiments, the direction 400 may be found based on computing an electrode contact level center of mass 402 (e.g., weighted center of mass) which is indicative of the overall direction of contact of the catheter electrodes 55. The direction 400 may then be found based on a line 404 connecting the electrode contact level center of mass 402 to a position-based center of mass 406 of the catheter electrodes 55. The position-based center of mass 406 is indicative of the center of mass of the catheter electrodes 55 without regard to the level of contact of the individual catheter electrodes 55.

Therefore, the processing circuitry 41 (FIG. 1) is configured to compute (block 308) the electrode contact level center of mass 402 of some or all of the catheter electrodes 55 responsively to the respective levels of contact and position coordinates of the respective catheter electrodes 55. For example, the electrode contact level center of mass 402 may be computed as a standard center of mass of any rigid body or bodies which is weighted according to the levels of contact of the catheter electrodes 55 included in the center of mass computation. The processing circuitry 41 is configured to find the direction 400 in which the catheter 40 should be moved responsively to the computed electrode contact level center of mass 402.

When each of the respective levels of contact is selected from respective two states of contact indicating an in-contact state with the tissue and a not-in-contact state with the tissue, the processing circuitry 41 is configured to compute the electrode contact level center of mass 402 of some or all of the catheter electrodes 55 responsively to the respective levels of contact having a same state (e.g., the electrodes which are all in-contact, or the electrodes which all not-in-contact) of the two states of contact. In other words, the electrode contact level center of mass 402 may be computed as the center of mass of the catheter electrodes 55 which have an in-contact state (e.g., electrodes 1-4, and 9-10). Alternatively, the electrode contact level center of mass 402 may be computed as the center of mass of the catheter electrodes 55 which have a not-in-contact state (e.g., electrodes 5-8).

When each of the respective levels of contact is selected from respective multiple states (e.g., at least three states) of quality of contact with the tissue, the processing circuitry 41 may be configured to compute the electrode contact level center of mass 402 of some or all of the catheter electrodes 55 as a weighted electrode contact level center of mass responsively to the respective levels of contact and the position coordinates of the respective catheter electrodes 55, with more weight being given to the catheter electrodes 55 with a higher quality of contact.

When each of the respective levels of contact is selected from a respective sliding scale of quality of contact with the tissue, the processing circuitry 41 may be configured to compute the electrode contact level center of mass 402 of some or all of the catheter electrodes 55 as a weighted electrode contact level center of mass responsively to the respective levels of contact, with more weight being given to the catheter electrodes 55 with a higher quality of contact.

The processing circuitry 41 is configured to compute (block 310) the position-based center of mass 406 of respective some or all of the catheter electrodes 55) responsively to the position coordinates of the respective catheter electrodes 55 (i.e., without regard to the level of contact of the individual catheter electrodes 55). The processing circuitry 41 is configured to find the direction 400 in which the catheter 40 should be moved responsively to the line 404 extending from the computed electrode contact level center of mass 402 to the computed position-based center of mass 406. The orientation of the direction 400 is generally parallel to the line 404 and points away from the electrode contact level center of mass 402.

The illustration of the catheter 40 in FIG. 4 shows a 2D view of the catheter 40. The above computations may be performed to compute a 3D direction 400 having an orientation in 3D space. For example, the electrode contact level center of mass 402, the line 404, and the position-based center of mass 406, may be computed in 3D space based on the 3D position coordinates of the catheter electrodes 55. The example of FIG. 4 is presented with respect to a balloon catheter. The direction 400 may be computed for any suitable catheter, for example, a basket catheter.

Figure 5:
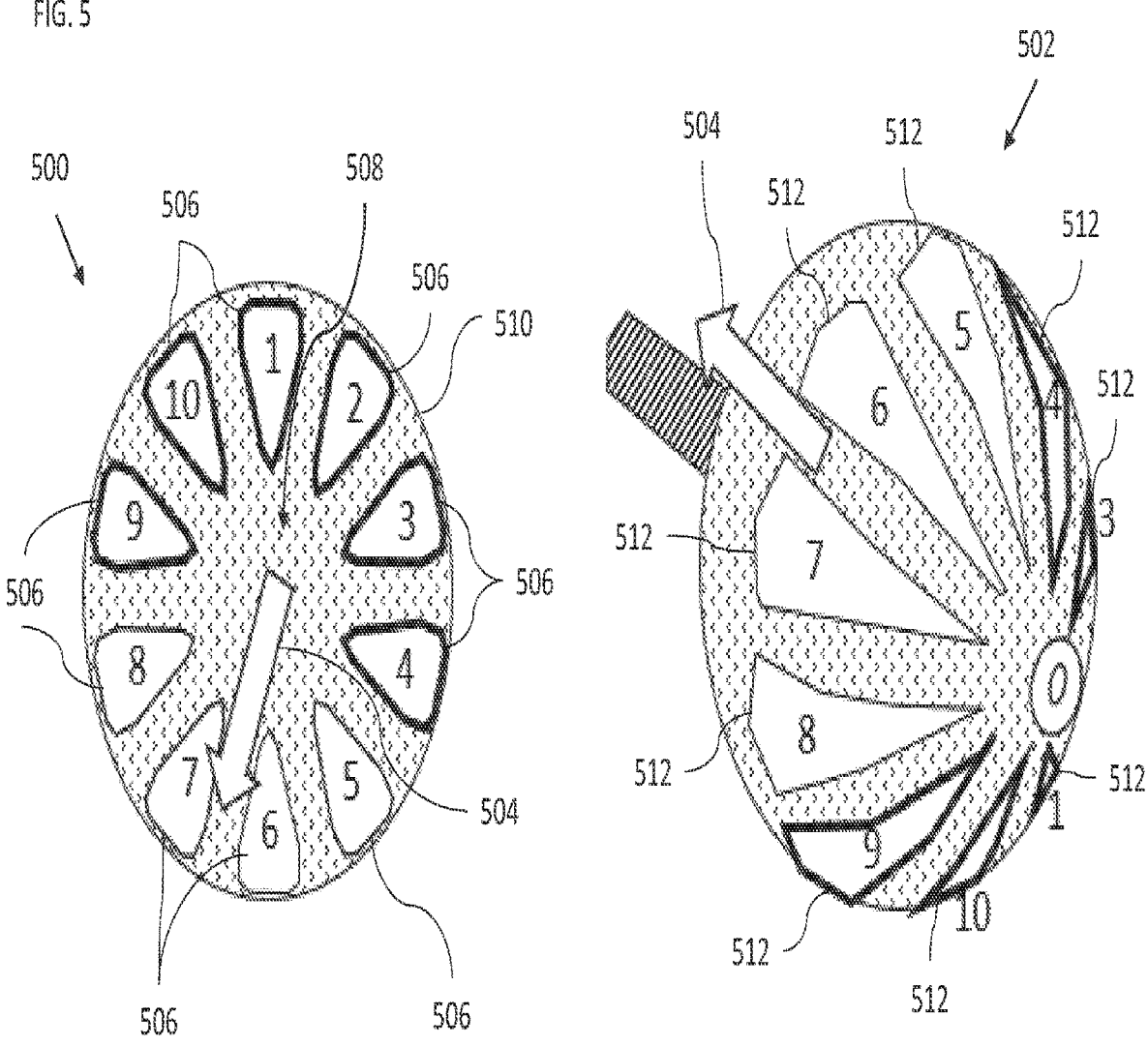
FIG. 5 is a schematic view showing a two-dimensional (2D) and three-dimensional (3D) representation of the balloon catheter of FIG. 2 and a superimposed direction indicator in 2D and 3D.

Reference is now made to FIG. 5, which is a schematic view showing a two-dimensional (2D) representation 500 and a three-dimensional (3D) representation 502 of the balloon catheter 40 of FIG. 2 and a superimposed direction indicator 504 in 2D and 3D. Reference is also made to FIG. 3.

The processing circuitry 41 (FIG. 1) is configured to render to the display 27 (FIG. 1): a representation (e.g., the 2D representation 500 and/or the 3D representation 502) of the catheter 40 responsively to the received signals (provided by the catheter 40 and which the processing circuitry 41 may use to compute position coordinates of the catheter 40 and the inflatable balloon 45); and the superimposed direction indicator 504 indicating the direction in which the catheter 40 should be moved responsively to the found direction 400 (FIG. 4).

The 2D representation 500 is a representation of the expandable distal end assembly (e.g. the inflatable balloon 45) of the catheter 40 showing a representation 506 of each of the catheter electrodes 55 (FIG. 2) disposed around the longitudinal axis of the catheter 40 with each of the catheter electrodes 55 extending from a central region 508 of the 2D representation 500 towards an outer perimeter 510 of the 2D representation 500. The representation 506 of each catheter electrode 55 in sufficient contact with tissue is highlighted with a thicker border.

The 3D representation 502 includes a representation 512 of each catheter electrode 55. The processing circuitry 41 is configured to render to the display 27 (FIG. 1) the 3D representation 502 of the catheter 40 with the direction indicator 504 in 3D space indicating the direction in which the catheter 40 should be moved in the 3D space.

Figure 6A:
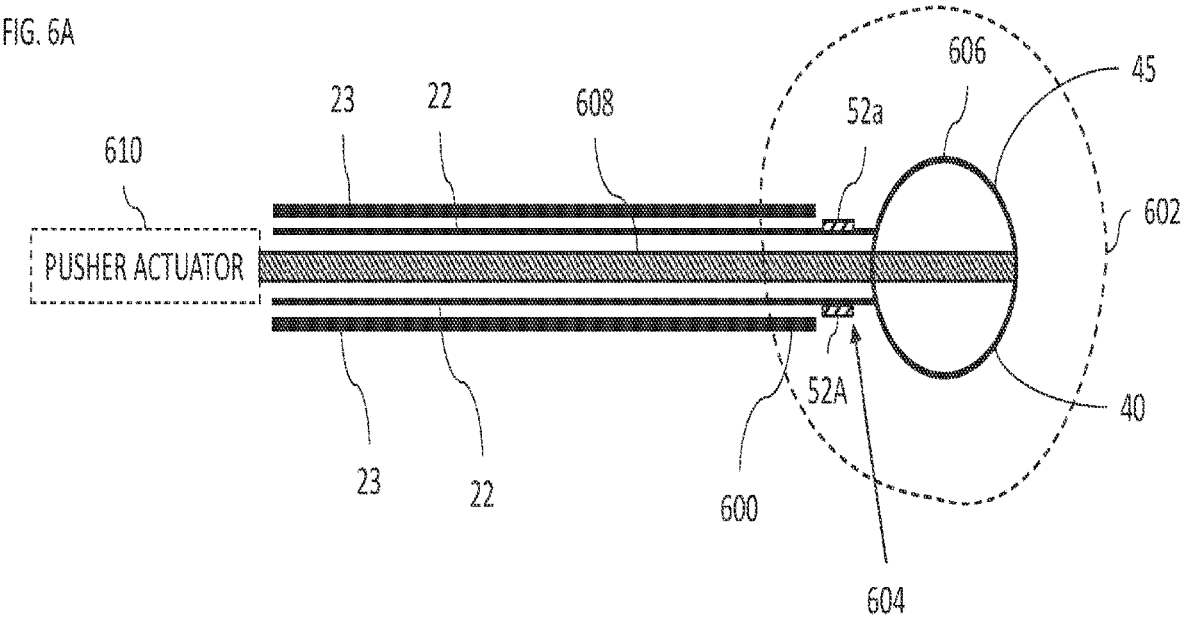
FIGS. 6A and 6B are schematic views of the balloon catheter of FIG. 2 in a deployed state and a collapsed state, respectively.
Figure 6B:
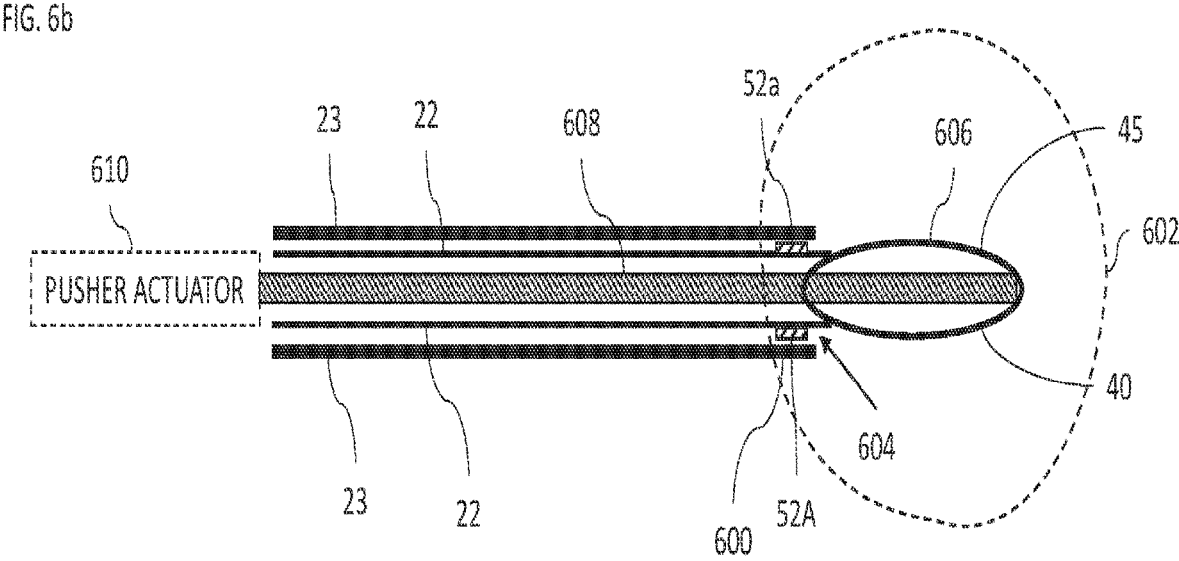

Reference is now made to FIGS. 6A and 6B, which are schematic views of the balloon catheter 40 of FIG. 2 in a deployed state and a collapsed state, respectively. Reference is also made to FIG. 7, which is a flowchart 700 including steps in a method for use in the system 20 of FIG. 1.

The sheath 23 has a distal end 600, and is configured to be inserted (block 702) into a body part 602 of a living subject (e.g., the patient 28 of FIG. 1). The shaft 22 of the catheter 40 has a distal portion 604, and an expandable distal end assembly 606 (e.g., the inflatable balloon 45) disposed distally to the distal portion 604. The catheter 40 is configured to be inserted (block 704) through the sheath 23 with the distal portion 604 and the expandable distal end assembly 606 protruding from the sheath 23 into the body part 602 (as shown in FIG. 6A). The catheter 40 includes a pusher 608 disposed in the shaft 22 and coupled to the expandable distal end assembly 606 such that adjusting the pusher 608 longitudinally with respect to the shaft 22 selectively elongates and shortens the expandable distal end assembly 606.

The position tracking sub-system 47 (FIG. 1) is configured to track (block 706) a relative position of the distal portion 604 of the shaft 22 and the distal end 600 of the sheath 23. At a decision block 708, the position tracking sub-system 47 is configured to determine if the distal portion 604 is currently in the distal end 600 of the sheath 23 responsively to the tracked relative position. If the distal portion 604 is not currently in the distal end 600 of the sheath 23 (branch 712), the position tracking sub-system 47 is configured to find (block 710) when the distal portion 604 of the shaft 22 enters the distal end 600 of the sheath 23 responsively to the tracked relative position. The system 20 includes a pusher actuator 610 configured to automatically actuate (block 714) the pusher 608 (on command from the position tracking sub-system 47) to elongate the expandable distal end assembly 606 responsibly to the distal portion 604 of the shaft 22 entering the distal end 600 of the sheath 23. Additionally, or alternatively, the sound outputting device 48 (FIG. 1) is configured to provide an audible alert (on command from the position tracking sub-system 47) responsibly to the distal portion 604 of the shaft 22 entering the distal end 600 of the sheath 23.

If the distal portion 604 is currently in the distal end 600 of the sheath 23 (branch 716), the position tracking sub-system 47 is optionally configured to find (block 718) when the distal portion 604 of the shaft 22 exits the distal end 600 of the sheath 23 responsively to the tracked relative position. The pusher actuator 610 is optionally configured to automatically actuate (block 720) the pusher 608 (on command from the position tracking sub-system 47) to shorten the expandable distal end assembly 606 responsibly to the distal portion 604 of the shaft 22 exiting the distal end 600 of the sheath 23. Additionally, or alternatively, the sound outputting device 48 is optionally configured to provide an audible alert (on command from the position tracking sub-system 47) responsively to the distal portion 604 of the shaft 22 exiting the distal end 600 of the sheath 23.

In some embodiments, the position tracking sub-system 47 comprises: the proximal electrode 52a disposed proximally to the expandable distal end assembly 606 on the distal portion 604 of the shaft 22; and body surface electrodes 49 (FIG. 1) configured to be attached to a skin surface of the living subject (e.g. the patient 28 of FIG. 1). The position tracking sub-system 47 is configured to track the relative position of the distal portion 604 of the shaft 22 and the distal end 600 of the sheath 23 responsively to a measured electrical impedance between the proximal electrode 52a and the body surface electrodes 49. The measured electrical impedance between the proximal electrode 52a and the body surface electrodes 49 being above a given limit is indicative of the proximal electrode 52a being covered by the sheath 23 and therefore the distal portion 604 of the shaft 22 is entering or is within the sheath 23.

Figure 8A:
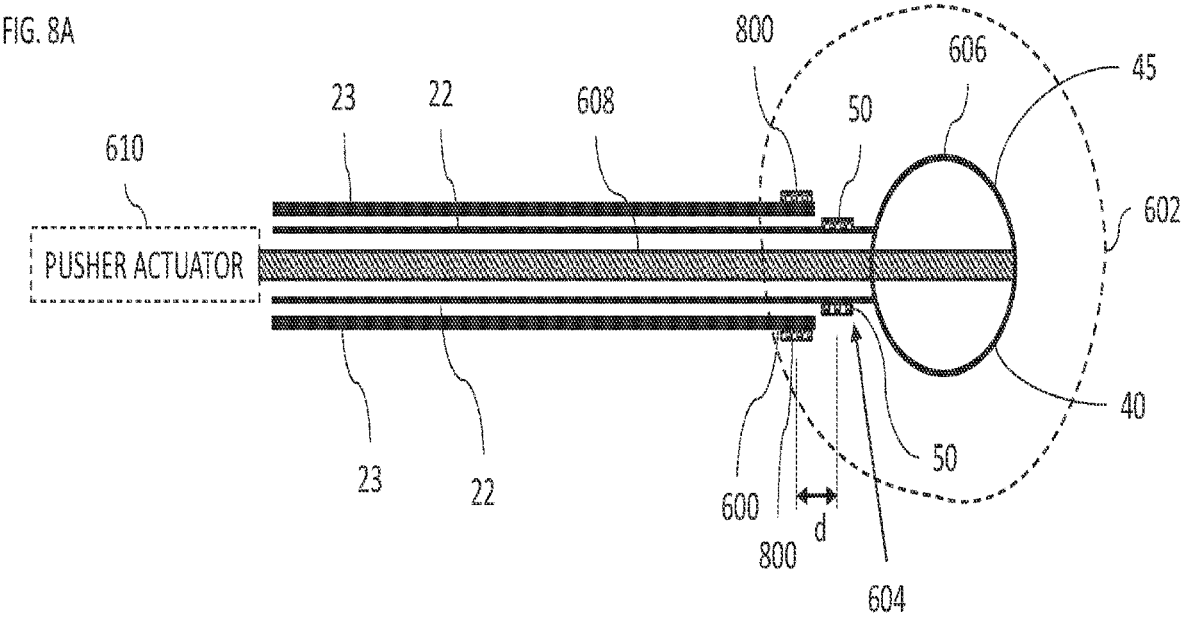
FIGS. 8A and 8B are schematic views of the balloon catheter of FIG. 2 in a deployed state and a collapsed state, respectively, disposed within a sheath having a magnetic coil sensor.
Figure 8B:
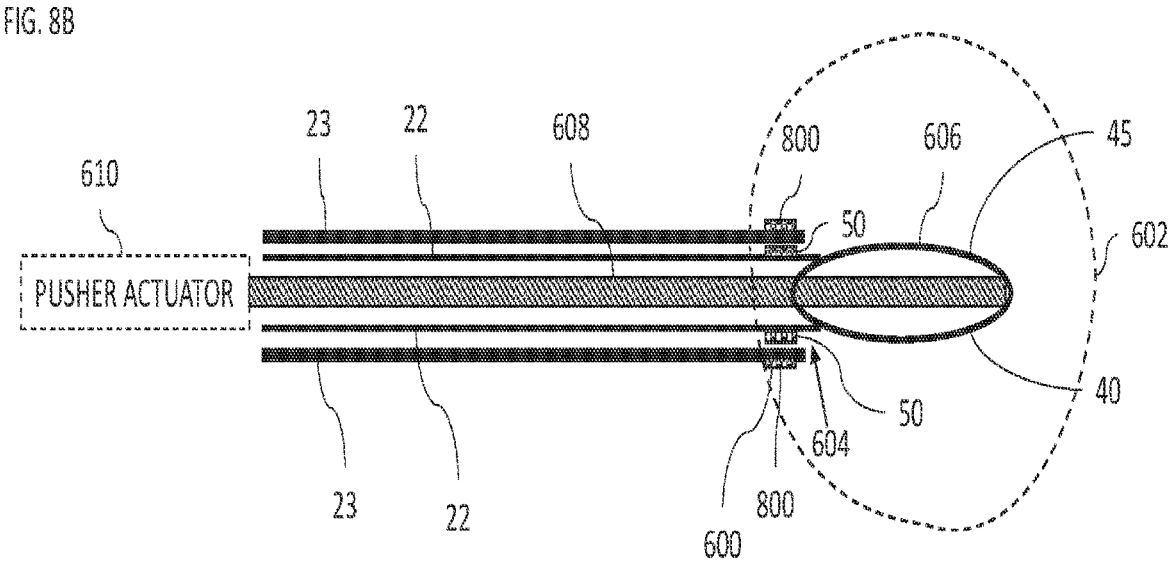
Figure 9:
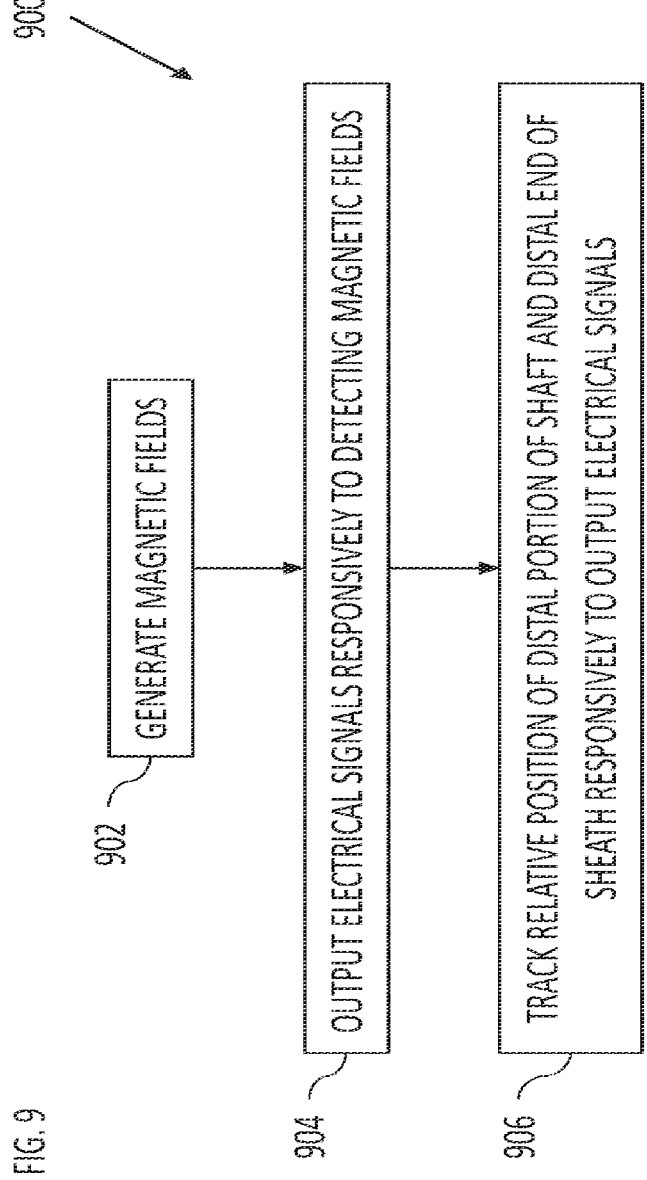
FIG. 9 is a flowchart showing steps in a method to track a relative position of the catheter and sheath of FIGS. 8A and 8B.

Reference is made to FIGS. 8A and 8B, which are schematic views of the balloon catheter 40 of FIG. 2 in a deployed state and a collapsed state, respectively, disposed within the sheath 23 having a magnetic coil sensor 800. Reference is also made to FIG. 9, which is a flowchart 900 showing steps in a method to track the relative position of the catheter 40 and sheath 23 of FIGS. 8A and 8B.

The position tracking sub-system 47 (FIG. 1) comprises: the magnetic field generator coils 42 (FIG. 1) configured to generate magnetic fields (block 902) having different frequencies in the body part 602; the magnetic coil sensor 50 disposed proximally to the expandable distal end assembly 606 (e.g., the inflatable balloon 45) at the distal portion 604 of the shaft 22; and the magnetic coil sensor 800 disposed at the distal end 600 of the sheath 23.

The magnetic sensor 50 and magnetic coil sensor 800 are configured to output (block 904) respective electrical signals responsively to detecting the magnetic fields generated by the magnetic field generator coils 42. The position tracking sub-system 47 is configured to track (block 906) the relative position of the distal portion 604 of the shaft 22 and the distal end 600 of the sheath 23, (e.g., the distance d in FIG. 8A) responsively to the output electrical signals.

The pusher actuator 610 is configured to automatically actuate the pusher 608 (on command from the position tracking sub-system 47 of FIG. 1) to elongate or shorten the expandable distal end assembly 606. Additionally, or alternatively, the sound outputting device 48 (FIG. 1) is configured to provide an audible alert, responsibly to the tracked relative position between the distal portion 604 and the distal end 600.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A catheter protection system, comprising:
a sheath having a distal end, and configured to be inserted into a body part of a living subject;
a catheter including a shaft having a distal portion, an expandable distal end assembly disposed distally to the distal portion, the catheter being configured to be inserted through the sheath with the distal portion and the expandable distal end assembly protruding from the sheath into the body part, the catheter including a pusher disposed in the shaft and coupled to the expandable distal end assembly such that adjusting the pusher longitudinally with respect to the shaft selectively elongates and shortens the distal end assembly;

a position tracking sub-system configured to: track a relative position of the distal portion of the shaft and the distal end of the sheath; and find when the distal portion of the shaft enters the distal end of the sheath responsively to the tracked relative position; and a pusher actuator configured to automatically actuate the pusher to elongate the expandable distal end assembly responsibly to the distal portion of the shaft entering the distal end of the sheath.

2. The catheter protection system according to claim 1, further comprising a sound outputting device configured to provide an audible alert responsively to the distal portion of the shaft entering the distal end of the sheath.

3. The catheter protection system according to claim 1, wherein:

the position tracking sub-system is configured to find when the distal portion of the shaft exits the distal end of the sheath responsively to the tracked relative position; and the pusher actuator is configured to automatically actuate the pusher to shorten the expandable distal end assembly responsibly to the distal portion of the shaft exiting the distal end of the sheath.

4. The catheter protection system according to claim 3, further comprising a sound outputting device configured to provide an audible alert responsively to the distal portion of the shaft exiting the distal end of the sheath.

5. The catheter protection system according to claim 1, wherein the position tracking sub-system comprises: generator coils configured to generate magnetic fields having different frequencies in the body part; a first magnetic coil sensor disposed proximally to the expandable distal end assembly at the distal portion of the shaft; and a second magnetic coil sensor disposed at the distal end of the sheath, the first and second magnetic coil sensors being configured to output respective electrical signals responsively to detecting the magnetic fields, the position tracking sub-system being configured to track the relative position of the distal portion of the shaft and the distal end of the sheath responsively to the output electrical signals.

6. The catheter protection system according to claim 1, wherein the expandable distal end assembly comprises an inflatable balloon.

7. The catheter protection system according to claim 1, wherein the expandable distal end assembly comprises a plurality of electrodes disposed thereon.

8. The catheter protection system according to claim 7, wherein the plurality of electrodes are configured to deliver ablative energy to tissue.

9. The catheter protection system according to claim 1, further comprising a force sensor configured to detect a force applied to the expandable distal end assembly.

10. A catheter protection system, comprising:

a sheath having a distal end, and configured to be inserted into a body part of a living subject;

a catheter including a shaft having a distal portion, an expandable distal end assembly disposed distally to the distal portion, the catheter being configured to be inserted through the sheath with the distal portion and the expandable distal end assembly protruding from the sheath into the body part, the catheter including a pusher disposed in the shaft and coupled to the distal end assembly such that adjusting the pusher longitudinally with respect to the shaft selectively elongates and shortens the distal end assembly;

a position tracking sub-system configured to: track a relative position of the distal portion of the shaft and the distal end of the sheath; and find when the distal portion of the shaft enters the distal end of the sheath responsively to the tracked relative position; and a sound outputting device configured to provide an audible alert responsibly to the distal portion of the shaft entering the distal end of the sheath.

11. The catheter protection system according to claim 10, wherein the position tracking sub-system comprises: a proximal electrode disposed proximally to the expandable distal end assembly on the distal portion of the shaft; and body surface electrodes configured to be attached to a skin surface of the living subject, the position tracking sub-system being configured to track the relative position of the distal portion of the shaft and the distal end of the sheath responsively to a measured electrical impedance between the proximal electrode and the body surface electrodes.

12. The catheter protection system according to claim 10, wherein:

the position tracking sub-system is configured to find when the distal portion of the shaft exits the distal end of the sheath responsively to the tracked relative position; and the sound outputting device is configured to provide another audible alert responsibly to the distal portion of the shaft exiting the distal end of the sheath.

13. The catheter protection system according to claim 10, wherein the position tracking sub-system comprises: a proximal electrode disposed proximally to the expandable distal end assembly on the distal portion of the shaft; and body surface electrodes configured to be attached to a skin surface of the living subject, the position tracking sub-system being configured to track the relative position of the distal portion of the shaft and the distal end of the sheath responsively to a measured electrical impedance between the proximal electrode and the body surface electrodes.

14. The catheter protection system according to claim 10, wherein the position tracking sub-system comprises: generator coils configured to generate magnetic fields having different frequencies in the body part; a first magnetic coil sensor disposed proximally to the expandable distal end assembly at the distal portion of the shaft; and a second magnetic coil sensor disposed at the distal end of the sheath, the first and second magnetic coil sensors being configured to output respective electrical signals responsively to detecting the magnetic fields, the position tracking sub-system being configured to track the relative position of the distal portion of the shaft and the distal end of the sheath responsively to the output electrical signals.

15. A catheter protection method, comprising:

inserting a sheath into a body part of a living subject;

inserting a catheter through the sheath with a distal portion of a shaft of the catheter and an expandable distal end assembly of the catheter protruding from the sheath into the body part;

adjusting a pusher disposed in the shaft, and coupled to the expandable distal end assembly, longitudinally with respect to the shaft to selectively elongate and shorten the expandable distal end assembly;

tracking a relative position of the distal portion of the shaft and the distal end of the sheath;

finding when the distal portion of the shaft enters the distal end of the sheath responsively to the tracked relative position; and automatically actuating the pusher to elongate the expandable distal end assembly responsibly to the distal portion of the shaft entering the distal end of the sheath.

16. The catheter protection method according to claim 15, further comprising providing an audible alert responsively to the distal portion of the shaft entering the distal end of the sheath.

17. The catheter protection method according to claim 15, further comprising:

finding when the distal portion of the shaft exits the distal end of the sheath responsively to the tracked relative position; and automatically actuating the pusher to shorten the expandable distal end assembly responsibly to the distal portion of the shaft exiting the distal end of the sheath.

18. The catheter protection method according to claim 17, further comprising provide an audible alert responsively to the distal portion of the shaft exiting the distal end of the sheath.

19. The catheter protection method according to claim 15, wherein the tracking comprises tracking the relative position of the distal portion of the shaft and the distal end of the sheath responsively to a measured electrical impedance between a proximal electrode disposed proximally to the expandable distal end assembly on the distal portion of the shaft and body surface electrodes attached to a skin surface of the living subject.

20. The catheter protection method according to claim 15, further comprising:

generating magnetic fields having different frequencies in the body part; and outputting respective electrical signals by a first magnetic coil sensor disposed proximally to the expandable distal end assembly at the distal portion of the shaft and a second magnetic coil sensor disposed at the distal end of the sheath responsively to detecting the magnetic fields, wherein the tracking comprises tracking the relative position of the distal portion of the shaft and the distal end of the sheath responsively to the output electrical signals.

* * * * *